United States Patent [19]
Glucksman

[11] Patent Number: 4,804,821
[45] Date of Patent: Feb. 14, 1989

[54] AROMA DIFFUSER ASSEMBLY

[75] Inventor: Dov Z. Glucksman, Brookline, Mass.

[73] Assignee: Environmental Fragrance Technologies, Ltd., New York, N.Y.

[21] Appl. No.: 65,840

[22] Filed: Jun. 23, 1987

Related U.S. Application Data

[63] Continuation-in-part of Ser. No. 878,096, Jun. 24, 1986, Pat. No. 4,731,520.

[51] Int. Cl.$^4$ ............................ H05B 3/06; A61L 9/03
[52] U.S. Cl. ........................................ 219/271; 219/276
[58] Field of Search ............... 219/271, 272, 273, 274, 219/275, 276, 521; 439/171, 172, 173, 174

[56] References Cited

U.S. PATENT DOCUMENTS

| | | | |
|---|---|---|---|
| 2,513,919 | 7/1950 | Costello | 219/272 |
| 2,611,068 | 9/1952 | Wellens | 439/174 |
| 2,690,501 | 9/1954 | Laibow | 219/275 |
| 2,841,695 | 7/1958 | Bentsen | 362/226 |
| 2,942,090 | 6/1960 | Diehl | 219/271 |
| 3,317,880 | 5/1967 | Meyer | 439/174 |
| 3,668,607 | 6/1972 | Farnworth | 439/139 |
| 4,037,901 | 7/1977 | Kaszuba | 439/138 |
| 4,370,010 | 1/1983 | Ordmandy | 439/174 |
| 4,384,756 | 5/1983 | Simonovich et al. | 439/53 |
| 4,391,781 | 7/1983 | van Lit | 219/274 |
| 4,467,177 | 8/1984 | Zobele | 219/271 |
| 4,631,387 | 12/1986 | Glucksman | 219/272 |

FOREIGN PATENT DOCUMENTS

| | | | |
|---|---|---|---|
| 232579 | 2/1959 | Australia | 219/271 |
| 936405 | 9/1963 | United Kingdom | |

*Primary Examiner*—E. A. Goldberg
*Assistant Examiner*—Teresa J. Walberg

[57] ABSTRACT

An aroma diffuser assembly is provided with an electrical wire heating element for effecting the release of an aroma from a contained aroma producing material. Power is supplied to the heating element by a power supply assembly which has a first portion for electrical connection to an external power source and a second portion for supplying power from the external power source to other than the heating element. The power supply assembly is rotational within the aroma diffuser assembly to accommodate both vertical and horizontal orientations of a conventional household outlet as a source of power.

36 Claims, 7 Drawing Sheets

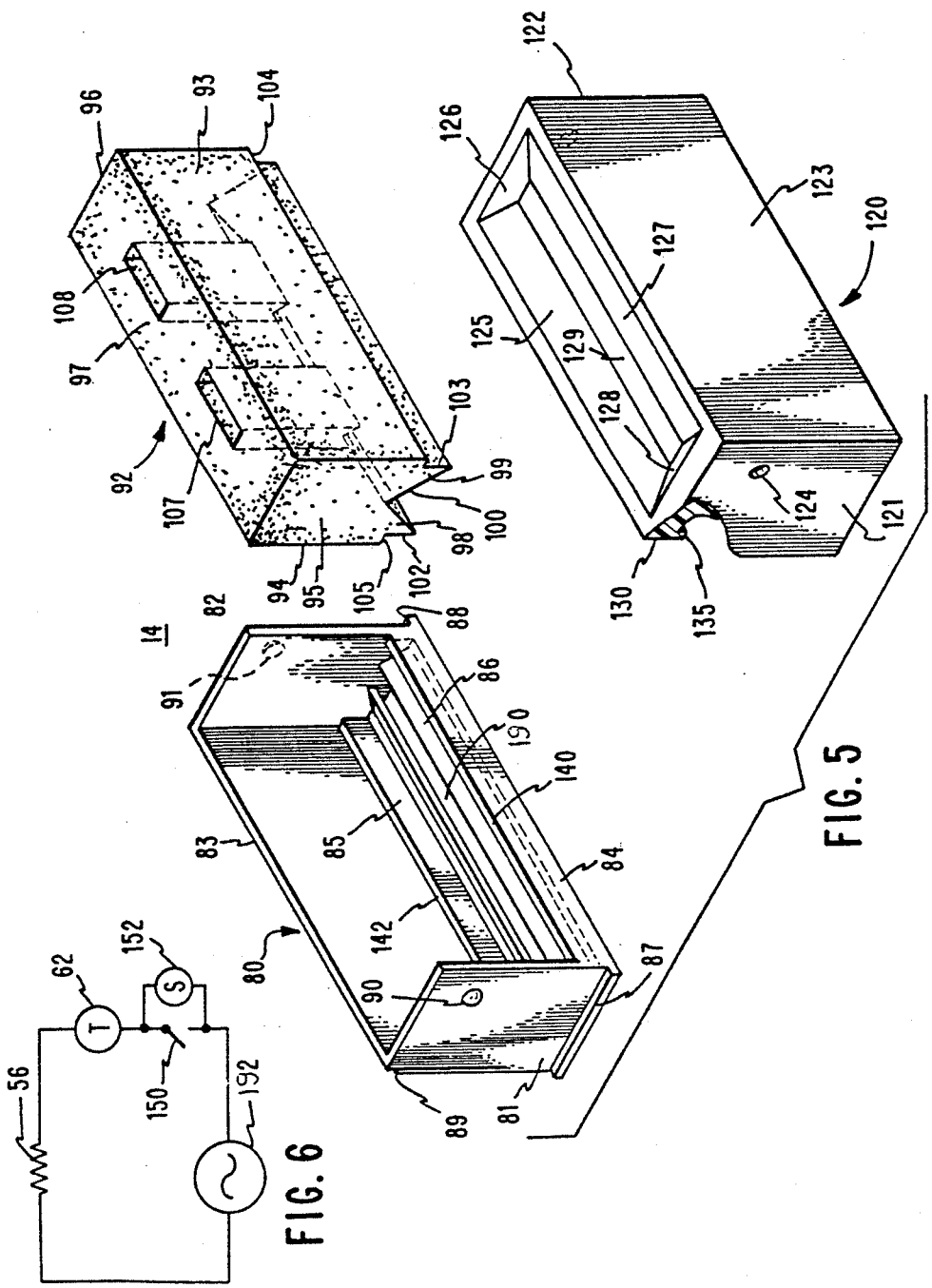

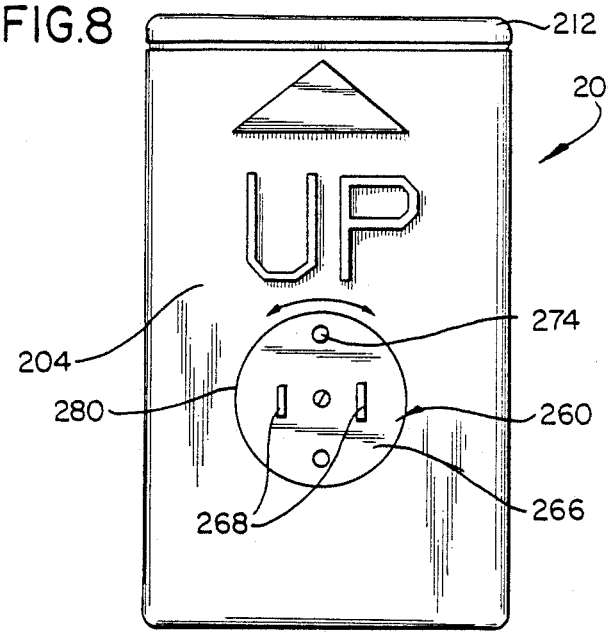
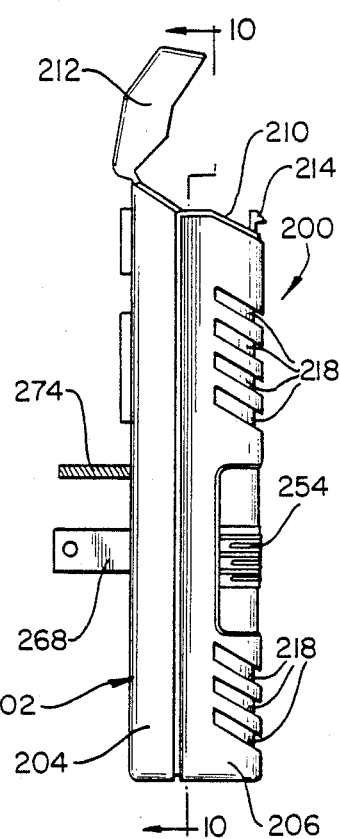
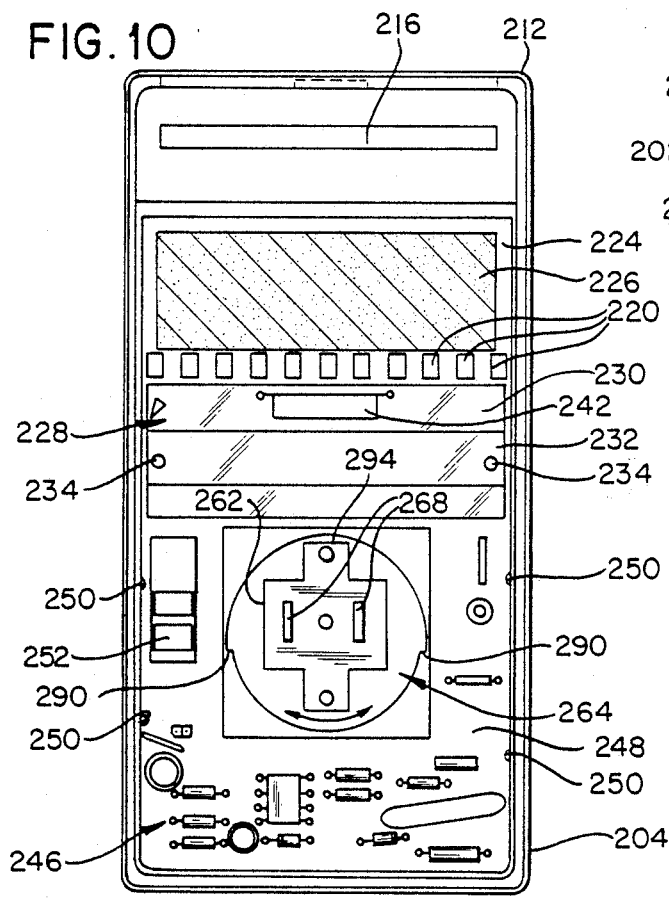

AROMA DIFFUSER ASSEMBLY

BACKGROUND OF THE INVENTION

This application is a Continuation-in-Part of U.S. Ser. No. 878,096 filed June 24, 1986 now U.S. Pat. No. 4,731,520.

The present invention relates in general to an aroma diffuser assembly, and more particularly, to an aroma diffuser assembly adapted for long term use in generating preselected aromas from replaceable aroma producing material contained within the assembly by means of an underlying electric heating element.

Many prior art devices exist wherein an electric light bulb in proximity to a liquid contained within a housing acts as the heating element to assist vaporization or evaporation of the liquid. See Gudeman, U.S. Pat. Nos. 1,403,548; Rosenthal, 1,706,939; Huff, 2,591,818; Diehl, 2,949,090; Weber III, 3,080,624; and Spector, 4,346,059. Other vaporizers are shown in Lockey, U.S. Pat. No. 658,793 and Messina, U.S. Pat. No. 2,515,310.

In Diehl, a housing containing a light bulb is adapted to be connected to a conventional wall plug receptacle. The housing includes means for supporting a number of deodorant disseminating tablets within the housing. Heat from the light bulb causes an air flow past the tablets thereby imparting an aroma to the air. When the tablets are exhausted, they can be replaced by removing the deodorizer from the outlet.

Alternative methods of generating aromas use aroma producing liquids sprayed or placed on an absorbent pad located above the heat source such as a light bulb. The liquid volatizes more quickly providing an instant aroma to the air when the unit is turned on. Heated air passes through the pad producing an aroma as it moves into the ambient atmosphere. In the Spector, U.S. Pat. No. 4,346,059, the liquid is confined within a bottle and is sprayed onto the pad when required in a controlled fashion.

More recently, aroma generating units which use an electrical heating element (other than a lamp) and disposable cartridge of some sort impregnated with the aromatic liquid to be dispersed have become popular. Aroma generating units of this type are shown in Costello, U.S. Pat. Nos. 2,513,919; Van Lit, 4,391,781; Moran, 3,895,928; Pons Pons, 4,425,302; Schimanski, 4,214,216; Spector, 4,571,485; Wellens, 2,611,068; Siebert, 2,756,322 and Yaffe, 2,931,880.

One such unit utilizes a flat circular cartridge adapted to be inserted horizontally into a slot within a housing. The unit contains a heating element below the slot. In Spector, U.S. Pat. No. 4,556,539, a disc playing aroma generator shows a disc formed of a circular sheet of absorbent material impregnated with a liquid fragrance and sandwiched between a pair of annular plastic films which are peripherally joined to create a central zone exposing the impregnated sheet. The disc is quite thin and the volume of liquid fragrance to be dispensed is limited by the disc shape.

Many other examples of aroma generating assemblies and devices exist. It is desirable, however, to provide an aroma diffuser assembly which is easy to use, uses aroma producing materials to provide the aroma but which avoids the complexity of handling aroma liquids to avoid the messiness associated therewith, and which provides a large quantity of aroma producing material to be dispensed for long term use.

SUMMARY OF THE INVENTION

In accordance with one embodiment of the present invention, there is disclosed an aroma diffuser assembly comprising a housing providing a cavity for receiving aroma producing material, heating means within the housing for effecting the release of an aroma from the aroma producing material, and power supply means for supply power to the heating means, the power supply means having a first portion for electrical connection to an external power source and a second portion for supplying power from the external power source to other than the heating means.

In accordance with another embodiment of the present invention, there is disclosed an aroma diffuser assembly comprising a housing providing a cavity for receiving aroma producing materials, heating means within the housing for effecting the release of aroma from the aroma producing material, and power supply means arranged within the opening of the housing for supplying power to the heating means, the power supply means shiftable between a first position releasably secured within the housing at a selected orientation and a second position within the housing permitting rotation of the power supply means between a plurality of orientations, and a projecting member extending from the housing and into the opening, the projecting member maintaining the power supply means at the first position and the second position, the power supply means shiftable between the first position and the second position upon application of a sufficient force to displace the power supply means from one side of the projecting member to the other side thereof.

BRIEF DESCRIPTION OF THE DRAWINGS

The above description, as well as further objects, features and advantages of the present invention will be more fully understood by reference to the following detailed description of the presently preferred, but nonetheless illustrative, aroma diffuser assembly in accordance with the present invention when taken in conjunction with the following drawings, wherein:

FIG. 5 is an exploded view of the cartridge assembly portion of the aroma diffuser assembly;

FIG. 6 is a block diagram schematic of an electrical circuit portion of the diffuser assembly of FIGS. 1 through 5;

FIG. 8 is a back elevational view of the aroma diffuser assembly of FIG. 7;

FIG. 9 is left side elevational view of the aroma diffuser assembly of FIG. 7;

FIG. 10 is a front cross-sectional view taken along the lines and arrows 10—10 in FIG. 9;

DETAILED DESCRIPTION

Figure 2:
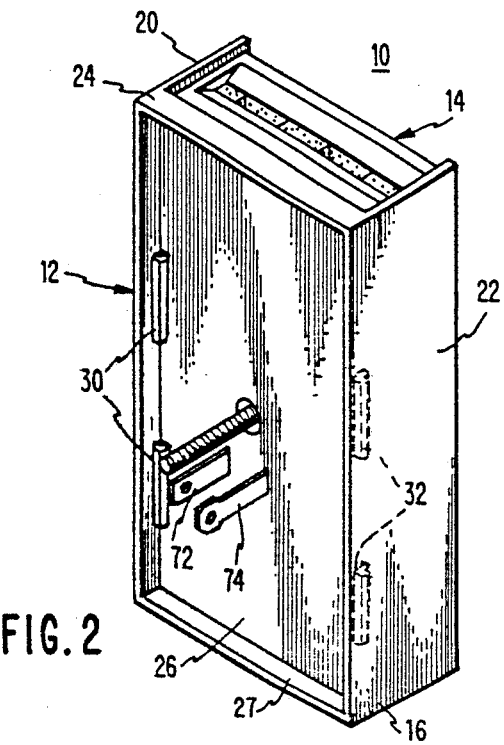
FIG. 2 is a back perspective view of the aroma diffuser assembly of FIG. 1.
Figure 4:
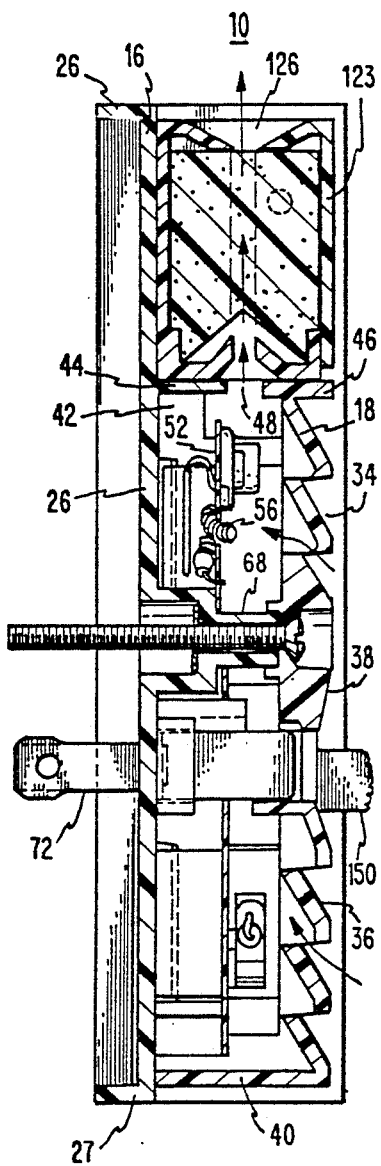
FIG. 4 is a side cross sectional view taken along the lines and arrows 4—4 in FIG. 3.
Figure 1:
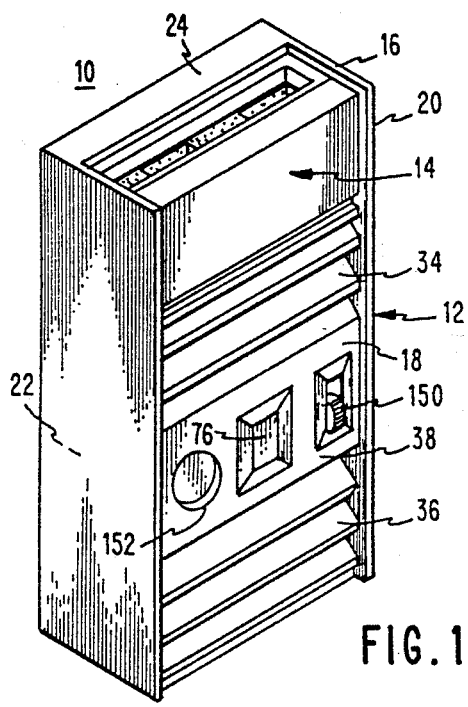
FIG. 1 is a front perspective view of an aroma diffuser assembly embodying the present invention.
Figure 3:
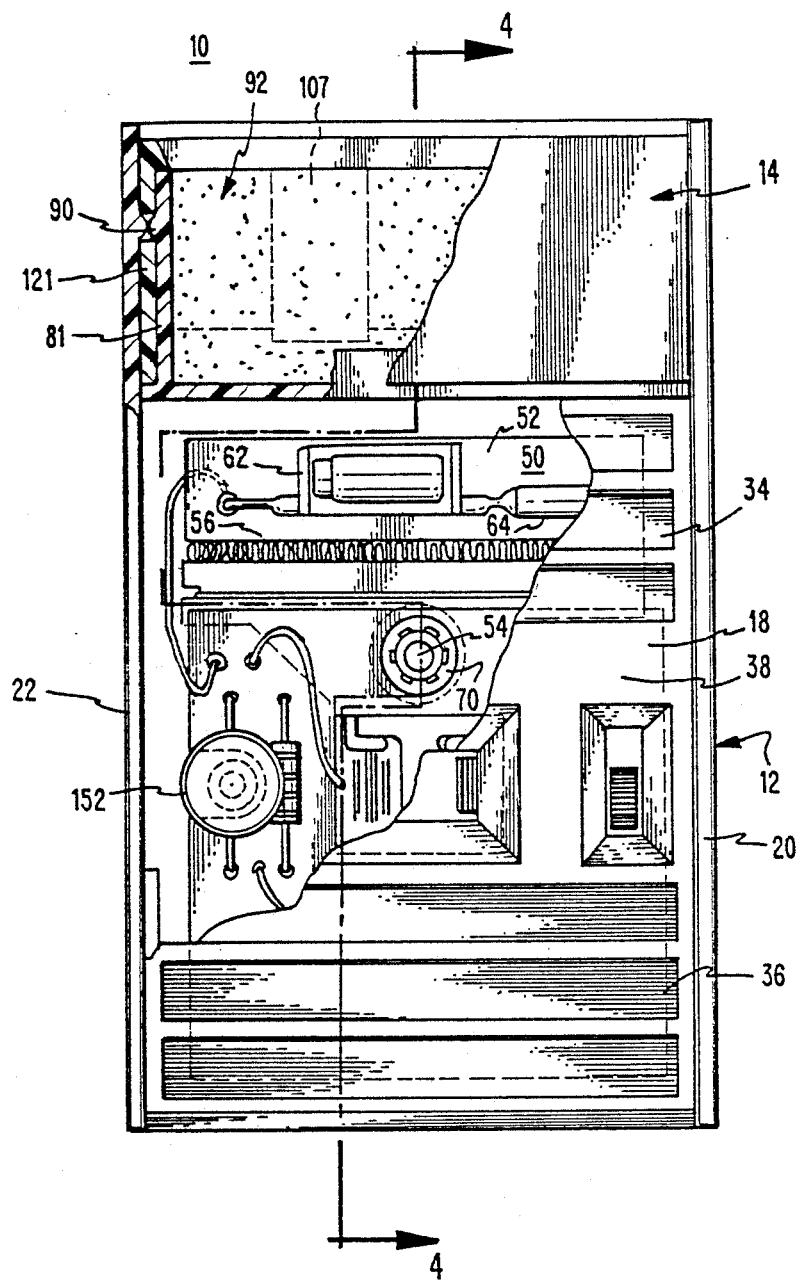
FIG. 3 is a front elevational view of the aroma diffuser assembly of FIG. 1 partially in cross section with the front shown partially broken away.

Referring now to the figures, wherein like reference numerals represent like elements, an aroma diffuser assembly designated generally 10 embodying the present invention comprises a housing 12 which supports an aroma dispensing cartridge designated generally 14. The housing 12 may be molded of suitable plastic material and in the preferred embodiment comprises a back plate 16 and a front cover 18.

The back plate comprises opposite side walls 20 and 22 connected by back side 26. The side walls extend past the back side 26 a short distance and the side walls are connected together at their top and bottom along the short distance by edges 24 and 27, respectively, all of which creates a recessed area in the back of the diffuser assembly. The back side 26 contains two pairs of slots adjacent the meeting of the back side 26 with the side walls 20 and 22, respectively. In the preferred embodiment, the back plate including the back side 26, side walls 20 and 22 and the edges 24 and 27 are integrally formed as one piece.

The front cover comprises a front surface with a first horizontally louvered area 34 spaced-apart from a second horizontally louvered area 36 by a flat surface 38. Each side edge of the front cover has a pair of tabs 30 and 32, respectively, which extend away from the front surface substantially perpendicular thereto. The tabs are adapted to snap into the pairs of slots in the back side 26 to attach the front cover to the back plate. The front surface of the front cover is integrally formed with a bottom surface 40 which extends perpendicularly away from the front surface in the same direction as the tabs.

When the two piece housing is snapped together it forms an interior compartment 42 formed by the front cover with front louvered surfaces 34 and 36, the bottom surface 40, and the side walls 20 and 22 and back side 26 of the back plate 16. At the top the compartment is formed by ledges 44 and 46. Ledge 44 is integrally formed with back side 26 and extends perpendicularly away therefrom toward the front cover. It is positioned below the edge 24 and is even with a horizontal ledge 46 at the top of front cover 18. The ledge 44 and ledge 46 are spaced-apart from one another to form a slot 48. The interior of compartment 42 communicates with ambient atmosphere through the louvered surfaces 34 and 36 on the front cover 18 and through the slot 48.

The aroma diffuser assembly further comprises a heater assembly designated generally 50 which comprises a metallic mounting plate 52 with a mounting hole 54, a 720 ohm rope heater element 56 wrapped around the mounting plate 52 and two wire leads for connecting the terminals of the heater element to a power source such as an AC outlet. A thermostat 62 and thermofuse 64 are coupled in series between one end of the rope element 56 and one of the wire leads. The back plate 16 comprises a post 68 integrally formed therewith and extending away from the back side 26 into the compartment 42. The heater assembly 50 is mounted to the back plate by inserting the post 68 through the mounting hole 54 in the plate and securing it thereto with star electrical outlet receptacle blades 72 and 74 which are mounted to the back plate 16 and which pass through slots in the back plate as shown in FIG. 2; hence, the entire aroma diffuser assembly 10 is adapted for connection to an electrical outlet.

Referring now to FIG. 5, details of the cartridge assembly 14 are shown in more detail. The cartridge assembly 14 comprises a cradle designated generally 80, an aroma block designated generally 92 and a cradle cover designated generally 120. The cradle is made of a suitable polymer such as polypropylene which is immune to attack from the various fragrances, etc. some of which are oil based and are to be diffused by the assembly 10. It comprises spaced-apart side walls 81 and 82 connected together by back wall 83. The front is open. The sides and back walls are integrally formed with a rectangular base 84 and extend upwardly therefrom. A pair of parallel and spaced-apart troughs 85 and 86 extend across the base 84 from one side wall 81 to the other 82. Trough 85 is adjacent to and engages the back wall 83 where it meets the base 84 while trough 86 runs along the front edge of base 84. The troughs are separated from one another forming a slot 190 in between in the bottom of the cradle. The base 84 extends outwardly from the side walls 81 and 82 to form side ledges 87 and 88 while the back wall 83 is reduced in thickness slightly at its top edge to form a ledge 89. Each side wall further comprises a bump 90 and 91 which protrude outwardly therefrom.

Aroma block 92 is preferably made of a porous plastic or polymer such as a porous polyethylene foam which is adapted to be impregnated with an oil base fragrance or other aroma producing chemical. The block is mostly rectangular in cross section with side walls 93 and 94, end walls 95 and 96 and top surface 97. The bottom of the block comprises a pair of parallel triangularly shaped protrusions 98 and 99 which run lengthwise along the block from end wall 95 to end wall 96. Where the sides of protrusions 98 and 99 meet they form an inverted V-shaped groove 100 extending inwardly into the bottom of the block. Sides 102 and 103 of protrusions 98 and 99 join the block 92 inwardly from the side walls 93 and 94 of the block to form a pair of spaced-apart and parallel longitudinal ledges 104 and 105.

The aroma block 92 further comprises a pair of rectangularly shaped channels 107 and 108 which extend from the apex of the inverted V-shaped groove at the bottom of the block to the top surface 97. The channels are open to ambient atmosphere at both ends and each is approximately 0.500 inches long and 0.125 inches wide. They are spaced apart from end walls 95 and 96 and lie generally along the center line between side walls 93 and 94.

The cradle cover 120 is also generally rectangular in shape and comprises a polymer such as polypropylene. It comprises end walls 121 and 122 joined by back wall 123. End walls 121 and 122 are equipped with a hole or indentation such as the hole 124 on end wall 121. The bottom is completely open a is the front opposite back wall 123. The top surface is formed with four sloping wall portions 125 through 128 which slope downwardly toward one another. They don't completely close off the top leaving a rectangular slot 129 whose largest dimension runs between end walls 121 and 122.

The sloping wall portion 125 rises up to meet a downwardly directed edge 130 which if extended would form a front wall of the cradle cover. The downwardly extending edge has a reduced thickness at tip 135 which extends downwardly below the slot 129.

To assemble the cartridge the aroma block is placed in the cradle with the triangularly shaped elongated protrusions 98 and 99 inserted in the troughs 85 and 86 with the ledges 104 and 105 of the protrusions resting on the top edges 140 and 142 of the troughs 86 and 85, respectively. Next, the cradle cover is slid into position around the block and cradle with the bottom edges of the end walls 121 and 122 resting on ledges 87 and 88 of the base. The cradle cover is snapped into place by forcing the bumps 90 and 91 on the end walls 81 and 82 of the cradle 80 to slip into holes 124 in the cradle cover 120 and forcing the tip 135 of the cover to snap over back wall 83 of the cradle. Room is made to accommodate the tip by ledge 89. The tolerances are such that the back wall 123 engages trough 86 along its length.

The cradle assembly is then placed into the recess in the top of the aroma assembly formed by the top portions of the side walls 20 and 22 and back side 26 of the aroma diffusion assembly 10 and ledges 44 and 46. The bottom of the troughs 85 and 86 at the perimeter of base 84 rests on the ledges 44 and 46 to support the cartridge assembly.

In use the aroma diffuser 10 is plugged into an ordinary 120 volt wall socket which is represented by the AC source 192 in FIG. 6. The aroma diffuser is turned on by switch 150 on the front cover, or in some models a light sensitive sensor 152 also found on the front cover and parallel with the switch 150 automatically turns on the aroma dispenser when the light in the room is turned on or at the presence of daylight. The rope heater 56 then heats up the ambient air within compartment 42. The heated air rises through slot 48, through slot 190 between troughs 85 and 86 where it is funneled by the V-shaped groove 100 into the channels 107 and 108 in the aroma block 92. Air is drawn into the compartment 42 through the louvered regions 34 and 36.

The aroma block should be made from a suitable material with good porosity which will absorb a good quantity of the aroma producing liquid and which will allow the liquid to vaporize as heated air passes through. In the preferred embodiment, the block is a porous, open cell polyethylene but open cell polymers or fibrous materials would also be suitable. The aroma producing liquid is either an essential fragrance oil, either single or in combination, or a chemical. The block can be impregnated in a variety of ways, e.g., by passing it through a solution or pressing the oil into the block under pressure. In the preferred embodiment a block when filled is expected to provide up to thirty hours or more of operation.

As heated air impinges upon the V-shaped groove it causes the aroma producing liquid in the block to vaporize. The V-shaped groove helps to funnel the heated air and vapors into the chimney like channels 107 and 108 where the heated air and vapors rise through the block 92 where further vaporization of the aroma producing liquid occurs. The chimney like openings are located directly beneath the slot 129 in the cradle cover so the heated air with aroma vapors passes therethrough into the open atmosphere. Only a slot is provided above the block since it is desirable to encapsulate the block as much as possible to avoid contact with hands or clothing by the liquid. But the aroma producing vapors in the heated air will condense against the surface of any enclosures causing dripping of the liquid down into the diffuser and possibly out the bottom of the diffuser onto the floor or rug etc. This is unsightly and undesirable.

The tolerances between the sizes of the block, cradle and cradle cover are made very close and the chimney channels are located just beneath the slot 129. This reduces the amount of vapor which will find its way between the block and the walls of the cradle and cover. Vapor which does condense on the interior walls of the cradle and cover, will run down and collect in the troughs 85 and 86 where it will be reabsorbed into the block through the triangularly shaped projections 98 and 99.

Figure 7:
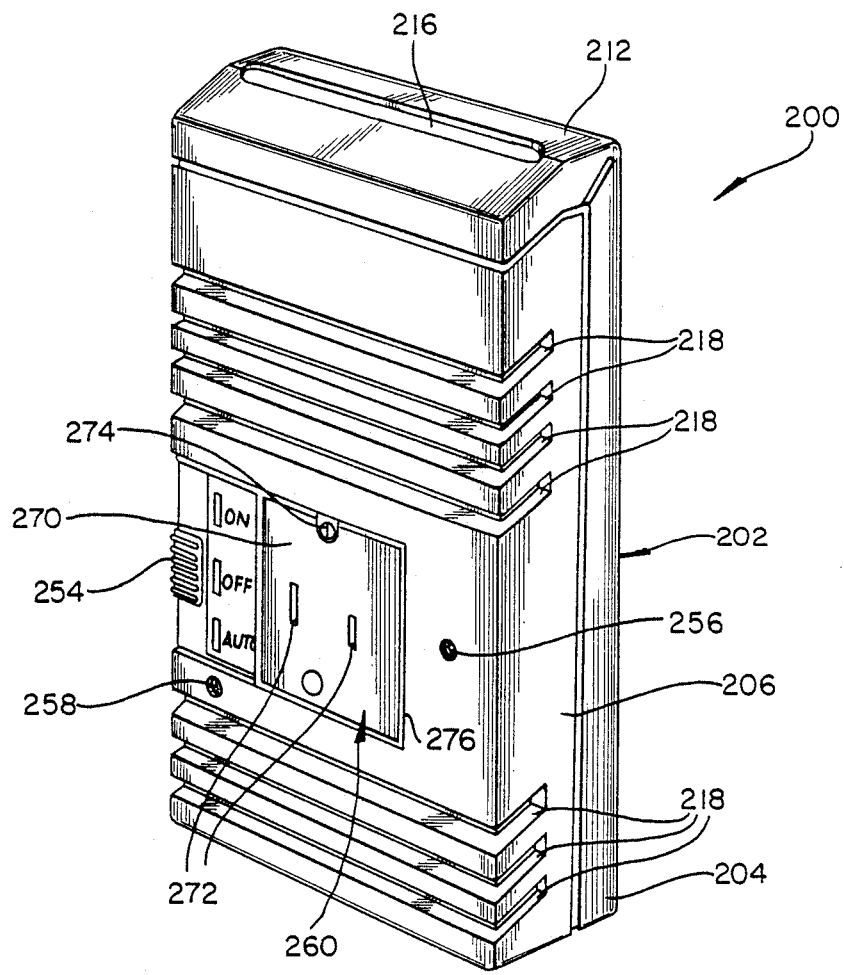
FIG. 7 is a front perspective view of an aroma diffuser assembly in accordance with another embodiment of the present invention.

Turning now to FIGS. 7, 8 and 9, there is disclosed an aroma diffuser assembly 200 constructed in accordance with another embodiment of the present invention. The aroma diffuser assembly 200 is constructed from a housing 202 generally formed of molded synthetic material such as rigid and semi-rigid plastic material. The housing 202 includes a back cover 204 and a matable front cover 206 which define a hollow region 206 (see FIG. 13) therebetween. The housing 202 is provided with an open top 210 (see FIG. 9) which is closable by means of a closure member 212 hinged to the back cover 204 and securable in a closed position by means of a locking member 214 attached to the front cover 206. The closure member 212 is provided with a longitudinally extending opening 216 to permit liberation of aromatic vapors from the contained aroma producing material as to be described hereinafter.

The front cover 206 is provided with a plurality of slotted openings 218 which provide for air convection through the interior of the housing 202 and out through the opening 216 within the closure member 212. As shown in FIG. 10, a plurality or ribs 220 extend inwardly from the back cover 204 to define a cavity 224 thereabove. A corresponding arrangement of ribs 220 (not shown) extend inwardly from the front cover 206. The cavity 224 is dimensioned to receive a block of aroma producing material 226 therein through the open top 210. The ribs 220 may be integrally formed with the back cover 204 and the front cover 206. As previously described, the aroma producing material 226 is preferably made of a porous plastic or polymer such as a porous polyethylene foam which is adapted to be impregnated with an oil based fragrance or other aroma producing chemicals.

Figure 11:
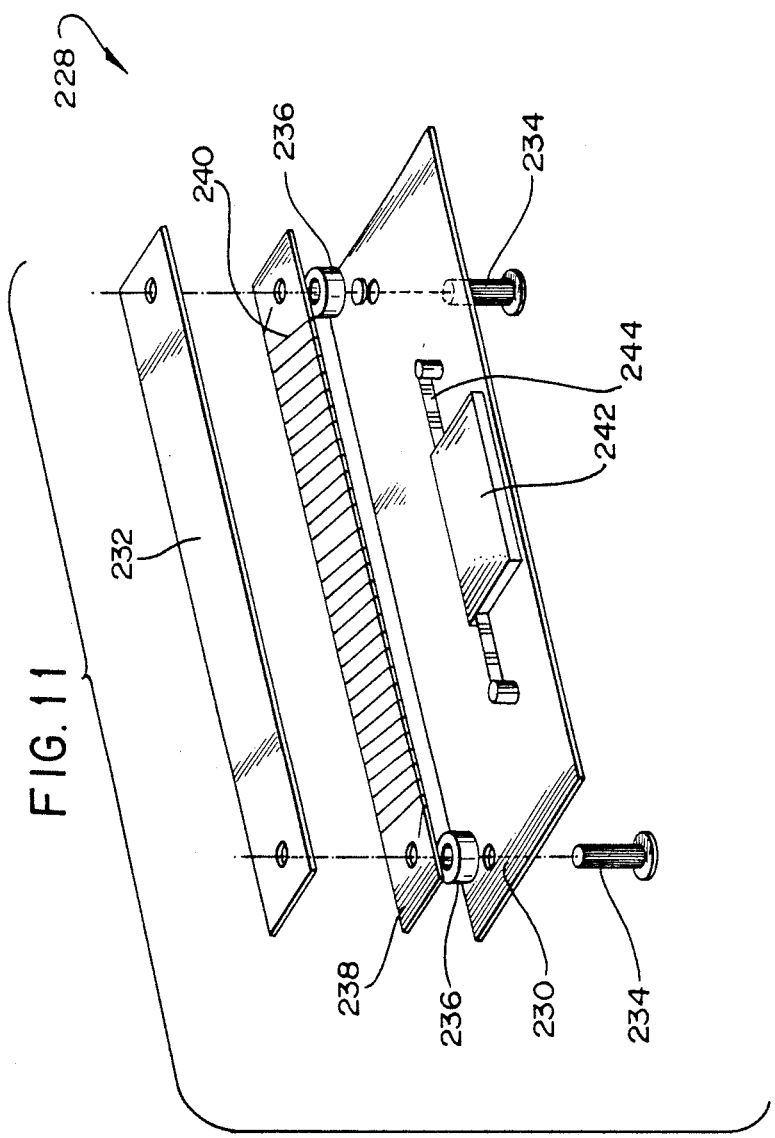
FIG. 11 is a exploded view of the heater assembly portion of the aroma diffuser assembly.

Referring to FIGS. 10 and 11, underlying the ribs 220, there is provided a heating element assembly 228. The heating element assembly 228 is constructed from a pair of spaced-apart mica plates 230, 232 by means of eyelets 234. The mica plates 230, 232 are held apart in spaced relationship by means of mica washers 236. Arranged between the mica plates 230, 232 and supported in fixed relationship by eyelets 234 and mica washers 236, is an additional mica plate 238 having a wound wire resistance heating element 240. The heating element 240 is electrically coupled in the manner previously described to a thermostat 242 which is arranged in series with a thermal fuse 244. The thermostat 242 is supported by the mica plate 230 and positioned directly underlying the ribs 220. In this manner, the temperature of the heated air directly underlying the aroma producing material 226 will be controlled by means of the thermostat 242 to the desired temperature. The mica plates 230, 232 function to channel air, being conveyed through the housing 202 by means of convection, over the heating element 240 and the exposed thermostat 242. In this manner, the heating element assembly 228 results in a more efficient and more precision controlled heating of the incoming air for accurately controlling the generation of aromas from the aroma producing material 226.

Electrical power to the heating element 240 is supplied by means of an electrical circuit generally designated by reference numeral 246, supported on a printed circuit board 248 arranged underlying the heater element assembly 228 within the housing 202. The circuit 246 may be as previously described with respect to FIG. 6 or with any other construction which supplies power either continuously or intermittently to the heating element 240. The printed circuit board 248 is secured within the housing 202 by means of a plurality of projections 250 extending inwardly from the side walls forming the back cover 204. A control switch 252 is mounted on the printed circuit board 248 for operation of the circuit 246 between an off mode, on mode and automatic mode. The control switch 252 is externally controlled to the desired mode by means of an external switch lever 254. An indicator light 256 is provided to indicate an on condition of the aroma diffuser assembly 200 and a photocell 258 is provided for automatic control of the circuit 246 in response to ambient light.

Power from an external source such as 120 volts AC, is supplied to the aroma diffuser assembly 200 by means of a power supply assembly 260. The power supply assembly 260, as best shown in FIGS. 7, 8, 13 and 14 includes a back boss 262 attached to a front boss 264. The back boss 262 includes an exposed circular member 266 through which extends a pair of electrical prongs 268 of the type adapted for electrical connection with a conventional household socket of 120 volts AC. The prongs 268 extend inwardly into the front boss 264, as illustrated by the dash lines in FIGS. 13 and 14. The front boss 264 include an exposed rectangular member 270 having a pair of spaced-apart slotted openings 272 (see FIG. 7). The slotted openings 272 are dimensioned and arranged for receiving a conventional 120 volt AC male plug. In this regard, the prongs 268 extend partially into the openings 272 to supply electrical power, i.e, 120 volts AC, from an external source to a male plug attached to the front boss 264.

In this manner, the aroma diffuser assembly 200 is electrically connected to a conventional household 120 volt AC outlet by inserting the prongs 268 thereinto. Typically, such outlets are of the multiple outlet type which allow for the connection to a number of appliances. Due to the size of the housing 202 of the aroma diffuser assembly 200, such other outlets are usually blocked to prevent access for plugging in other appliances and the like. To this end, the front boss 262, via openings 272, allow for the connection of other electrical appliances and the like to the outlet for receiving power therefrom. In other words, the power supply assembly 260, in addition to supplying electrical power to the heat element assembly 228, also provides an accessory outlet for powering other appliances and the like. The aroma diffuser assembly 200 may be secured to the household outlet by means of a threaded screw 274 which extends through the housing 202 and rearwardly thereof.

As thus far described, the aroma diffuser assembly 200 is electrically connected to conventional housing outlets for receiving 120 volts AC. In connecting the aroma diffuser assembly, it is preferable that the housing 202 be arranged in a substantially vertical orientation, as shown in FIG. 7. This vertical orientation is preferred to maximizing the drafting effect of outside air through the housing via openings 218 in the front cover 206 and opening 216 within the closure member 212. Unfortunately, household outlets are not always vertically arranged, sometimes being arranged horizontally. As such, this would result in the aroma diffuser assembly 200 being arranged in a corresponding horizontal orientation thereby hampering the effectiveness of its operation. To this end, the power supply assembly 260 is constructed and arranged to be rotatable within the housing 202, to allow the aroma diffuser assembly 200 to be installed in a vertical orientation independent of the orientation of the household outlet.

Referring to FIGS. 10 and 12-14, the front cover 206 is provided with a rectangular opening 276 having a surrounding lip 278. The rectangular member 270 of the front boss 264 is dimensioned to be received in slight interference fit within the confines of the surrounding lip 278 which forms the rectangular opening 276. The engagement of the rectangular member 270 with the lip 278 precludes rotation and inward movement of the front boss 264 within the hollow region 208 of the aroma diffuser assembly 200.

Figure 12:
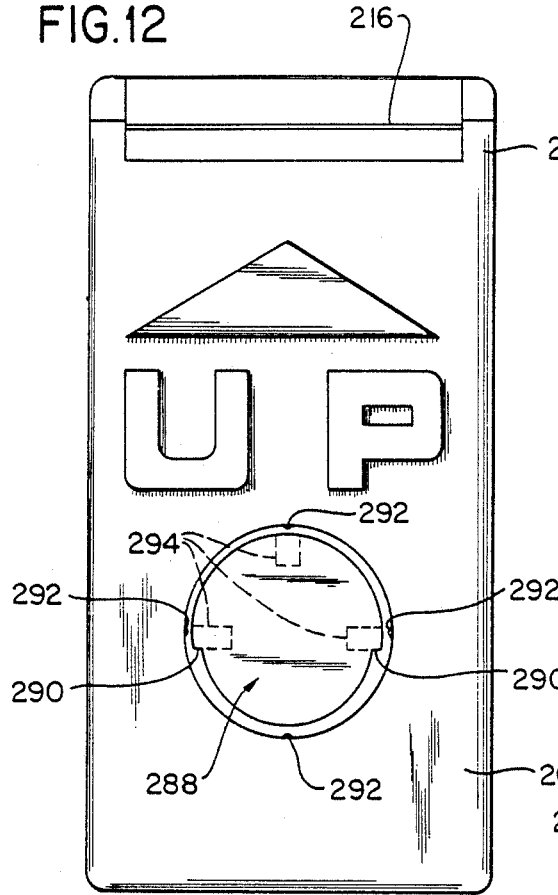
FIG. 12 is a back elevational view of the housing of the aroma diffuser assembly of FIG. 7.

The back cover 204 is provided with a circular opening 280 sized to receive in slight interference fit the circular member 266. Extending inwardly from the opening 280 and formed from a portion of the back cover 204 is a circular appendage 282. The appendage 282 is provided with a circular flange 284 extending about the top half of the appendage 282. A similar circular flange 286 extends about the lower half of the appendage 282. As best shown in FIG. 12, the flanges 284, 286 provides circular opening 288 which receives the back boss 262 of the power supply assembly 260. As further shown, the radius of the flange 284 is greater than the radius of the flange 286 so as to provide a pair of stop abutments 290 just below the horizontal axis of the opening 288. A plurality of spaced-apart projections 292 are provided inwardly extending into the opening 288 forward of the appendage 282 and inward of the outer surface of the back cover 204. As shown in FIG. 10, the back boss 262 is provided with a radially extending boss member 294. The radial outward extent of the boss member 294 from the central axis of the power supply assembly 260 is slightly less than the radius of flange 284, while being slightly greater than the radius of flange 286. The procedure for rotating the power supply assembly 260 to reorient the prongs 268 will now be described.

Figure 13:
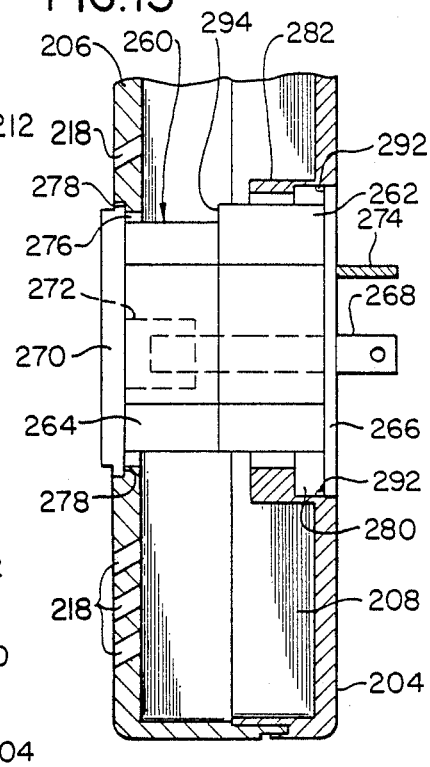
FIGS. 13 and 14 are partial side cross-sectional views showing the construction of the power supply means of the aroma diffuser assembly of FIG. 7.

Referring specifically to FIG. 13, the power supply assembly 260 is initially arranged within the aroma diffuser assembly 200 as shown. That is, the rectangular member 270 of the front boss 264 is engaged within the rectangular opening 276 by means of the lip 278. In this arrangement, the power supply assembly 260 is precluded from rotation due to the rectangular shape of the rectangular member 270 and its mating within the rectangular opening 276. On the opposite side of the housing 202, the projections 292 engage the rear surface of the circular member 266 of the back boss 262. This engagement prevents inadvertent lateral shifting of the power supply assembly 260. The arrangement of the power supply assembly 260, as shown in FIG. 13, is for mounting the aroma diffuser assembly 200 when the household outlet is conventionally arranged in the vertical orientation.

Figure 14:
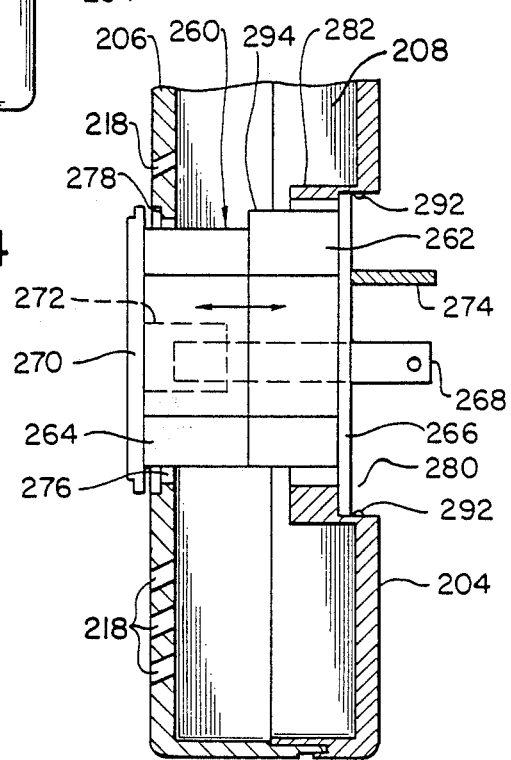

When it is desired to rotate the power supply assembly 260 as to accommodate a household outlet having a horizontal orientation, the power supply assembly is shifted laterally to the left along its rotational axis as shown in FIG. 14. A sufficient force must be applied to the circular member 266 of the back boss 262 to overcome the frictional engagement with the projections 292. As the power supply assembly 260 is shifted to the left, the circular member 266 engages the appendage 282 to prevent further lateral shifting, while the rectangular member 270 of the front boss 264 moves outward of the housing 202. In this position, the rectangular member 270 is free of its interference fit within the rectangular opening 276 within the front cover 206. The circular member 266 is now positioned to the left of the projections 292.

The power supply assembly 260 may now be rotated 90° clockwise, or 90° counterclockwise, to accommodate the horizontal orientation of the household outlet. As shown by the dashed lines in FIG. 12, the boss member 294 of the power supply assembly 260 was originally positioned along a vertical axis. The power supply assembly 260 may be rotated 90° clockwise until the boss member 294 engages the right stop abutment 290. Similarly, the power supply assembly 260 may be rotated 90° counterclockwise until the boss member 294 engages the left stop abutment 290. The stop abutments 290 prevent rotation of the power supply assembly 260 more than 90° in a clockwise or counterclockwise direction. Once the boss member 294 engages the stop abutment 290, the rectangular member 270 is now in registration with the rectangular opening 276 to be received therein. The lateral shifting of the power supply assembly 260 to the right will reposition the power supply assembly 260 into a secured orientation.

Although the invention herein has been described with reference to particular embodiments, it is to be understood that these embodiments are merely illustrative of the principles and applications of the present invention. It is to be understood that numerous modifications may made in the illustrative embodiments and other arrangements may be devised without departing from the spirit and scope of the present invention as defined by the appended claims.

I claim:

1. An aroma diffuser assembly comprising a housing providing a cavity for receiving aroma producing material, heating means within said housing for effecting the release of an aroma from the aroma producing material, and power supply means for supplying power to said heating means, said power supply means having a first portion for electrical connection to an external power source and a second portion having connecting means for supplying power from said external power source through said housing to an external power consuming apparatus when engaged with said connecting means, said power being supplied to said connecting means independent of the supplying of said power to said heating means.

2. The assembly of claim 1, further including aroma producing material received within said cavity.

3. The assembly of claim 1, wherein said housing includes an openable top for providing access to said cavity.

4. The assembly of claim 1, wherein said heating means is arranged underlying said cavity.

5. The assembly of claim 4, wherein said heating means comprises a pair of spaced-apart members providing a vertical opening therebetween, a heating element disposed between said members, and a temperature regulator arranged within said vertical opening above said heating element.

6. The assembly of claim 1, wherein said housing includes a plurality of inwardly projecting ribs for supporting the aroma producing material.

7. The assembly of claim 1, wherein said power supply means is rotatable between a first position and a second position to maintain said housing in a preselected orientation.

8. The assembly of claim 7, wherein said first position and said second position are approximately 180° apart.

9. The assembly of claim 7, wherein said housing includes stop means for engaging a portion of said power supply means to prevent the further rotation thereof when arranged in said first position or said second position.

10. The assembly of claim 7, wherein said power supply means is shiftable with respect to said housing between a first location whereby said power supply means is prevented from rotation and a second location, whereby said power supply means is rotatable about its axis.

11. The assembly of claim 10, wherein said first portion of said power supply means is located within said housing and said second portion of said power supply means is located outside said housing when said power supply means is arranged in said second location.

12. The assembly of claim 11, wherein said first portion of said power supply means comprises a circular member and said second portion of said power supply means comprises a rectangular member, said circular member received within a corresponding circular opening within said housing and said rectangular member received within a corresponding rectangular opening within said housing when said power supply means is arranged within said first location.

13. The assembly of claim 12, wherein said rectangular opening is formed of a portion of said housing having means for preventing the inward movement of said rectangular member.

14. The assembly of claim 12, wherein said circular opening is formed of a portion of said housing having means for limiting the inward movement of said circular member.

15. The assembly of claim 14, wherein a portion of said housing forming said circular opening includes stop means for engaging a portion of said power supply means to limit the extent of rotation of said power supply means.

16. The assembly of claim 10, wherein said housing includes positioning means for positioning said power supply means in said first location.

17. The assembly of claim 16, wherein said positioning means includes plurality of projecting members engaging said first portion of said power supply means.

18. The assembly of claim 17, wherein said first portion of said power supply means is shiftable to said second location upon application of a sufficient force to displace said first portion from one side of said projecting members to the other side thereof inwardly of said housing, whereby said power supply means may be rotated about its axis.

19. An aroma diffuser assembly comprising a housing providing a cavity for receiving aroma producing material, heating means within said housing for effecting the release of aroma from the aroma producing material, and power supply means arranged within an opening of said housing for supplying power to said heating means, said power supply means shiftable between a first location releasably secured within said housing at a selected orientation and a second location within said housing permitting rotation of said power supply means between a plurality of orientations, and a projecting member extending from said housing and into said opening, said projecting member maintaining said power supply means at said first location and said second location, said power supply means shiftable between said first location and said second location upon application of a sufficient force to displace said power supply means from one side of said projecting member to the other side thereof.

20. The assembly of claim 19, wherein said heating means comprises a pair of spaced-apart members providing a vertical opening therebetween, a heating element disposed between said members, and a temperature regulator arranged within said vertical opening above said heating element.

21. The assembly of claim 19, further including aroma producing material received within said cavity.

22. The assembly of claim 19, wherein said power supply means is rotatable between a first position and a second position to maintain said housing in a preselected orientation.

23. The assembly of claim 22, wherein said housing includes stop means for engaging a portion of said power supply means to prevent the further rotation thereof when arranged in said first position or said second position.

24. The assembly of claim 19, wherein said power supply means includes a circular member and a rectangular member, said circular member received within a corresponding circular opening within said housing and said rectangular member received within a corresponding rectangular opening power supply means when in said first location.

25. An aroma diffuser assembly comprising a housing providing a cavity for receiving aroma producing material, heating means within said housing for effecting the release of aroma from the aroma producing material, and power supply means arranged within an opening of said housing for supplying power to said heating means, said power supply means shiftable between a first location releasably secured within said housing at a first orientation and a second location permitting rotation of said power supply means to a second orientation, said power supply means being releasably secured within said housing at said second orientation upon shifting said power supply means to said first location from said second location.

26. The assembly of claim 25, wherein said heating means comprises a pair of spaced-apart members providing a vertical opening therebetween, a heating element disposed between said members, and a temperature regulator arranged within said vertical opening above said heating element.

27. The assembly of claim 25, further including aroma producing material received within said cavity.

28. The assembly of claim 25, wherein said housing includes stop means for engaging a portion of said power supply means to prevent the further rotation thereof when arranged in said first orientation or said second orientation.

29. The assembly of claim 25, wherein said power supply means includes a circular member and a rectangular member, said circular member received within a corresponding circular opening within said housing and said rectangular member received within a corresponding rectangular opening within said housing, thereby preventing rotation of said power supply means when in said first location.

30. The assembly of claim 29, wherein said rectangular opening is formed of a portion of said housing having means for preventing the inward movement of said rectangular member.

31. The assembly of claim 30, wherein said circular opening is formed of a portion of said housing having means for limiting the inward movement of said circular member.

32. The assembly of claim 31, wherein a portion of said housing forming said circular opening includes stop means for engaging a portion of said power supply means to limit the extent of rotation of said power supply means.

33. The assembly of claim 31, wherein said housing includes positioning means for position said power supply means in said first location.

34. The assembly of claim 33, wherein said positioning means includes plurality of projecting members engaging said circular member of said power supply means.

35. The assembly of claim 34, wherein said circular member of said power supply means is shiftable to said second location upon application of a sufficient force to displace said circular member from one side of said projecting members to the other side thereof inwardly of said housing, whereby said power supply means may be rotated about its axis.

36. An aroma diffuser assembly comprising a housing providing a cavity for receiving aroma producing material, heating means within said housing for effecting the release of an aroma from the aroma producing material, and power supply means for supplying power to said heating means, said power supply means having a portion for electrical connection to an external power source, said power supply means rotatable between a first position and a second position to maintain said housing in a preselected orientation, said power supply means shiftable with respect to said housing between a first location whereby said power supply means is prevented from rotation and a second location whereby said power supply means is rotatable about its axis.

* * * * *